(12) United States Patent
Topp et al.

(10) Patent No.: US 7,727,139 B2
(45) Date of Patent: Jun. 1, 2010

(54) DREAM DETECTION SYSTEM

(76) Inventors: Daniel Topp, 7495 Pyrite Way, Castle Rock, CO (US) 80108; Kimberly Viera, 20535 E. Girard Pl., Aurora, CO (US) 80013

( * ) Notice: Subject to any disclaimer, the term of this patent is extended or adjusted under 35 U.S.C. 154(b) by 667 days.

(21) Appl. No.: 11/551,471

(22) Filed: Oct. 20, 2006

(65) Prior Publication Data
US 2008/0114263 A1    May 15, 2008

(51) Int. Cl.
*A61M 21/00*    (2006.01)
(52) U.S. Cl. .......................................... 600/27; 351/209
(58) Field of Classification Search ............. 600/26–28, 600/544–546, 558, 595; 128/897–898; 351/209–210
See application file for complete search history.

(56) References Cited

U.S. PATENT DOCUMENTS

| | | | |
|---|---|---|---|
| 3,774,593 A * | 11/1973 | Hakata et al. ............... | 600/544 |
| 4,735,199 A * | 4/1988 | DiLullo ....................... | 600/28 |
| 4,863,259 A * | 9/1989 | Schneider et al. ........... | 351/210 |
| 5,507,716 A | 4/1996 | Laberge et al. | |
| 5,551,879 A | 9/1996 | Raynie et al. | |
| 6,540,664 B1 * | 4/2003 | Blair .......................... | 600/27 |
| 6,928,031 B1 * | 8/2005 | Kanevsky et al. ............. | 368/12 |
| 7,148,611 B1 * | 12/2006 | Liu ............................. | 310/366 |
| 2006/0293608 A1 * | 12/2006 | Rothman et al. ............ | 600/545 |

* cited by examiner

*Primary Examiner*—John P Lacyk
(74) *Attorney, Agent, or Firm*—Dale J. Ream

(57) ABSTRACT

A dream detection system includes a mask and a control unit. The mask includes opaque eye portions and at least one sensor for detecting REM sleep. The mask may include an alarm for indicating REM sleep, a speaker, and a transmitter. The control unit includes a receiver and transmitter for receiving data from and transmitting data to the mask, respectively. The control unit includes programming for actuating an audio player to provide a predetermined cue, script, or other audible message to the mask when REM sleep is detected for alerting a sleeping person that he is dreaming and enabling the person to gain some level of control over the dream sequence. The audible message may be a morning or evening affirmation, preparation for a task, or other cues to guide a dream. The control unit may include a device with which a user may audibly record dream details.

11 Claims, 7 Drawing Sheets

DREAM DETECTION SYSTEM

BACKGROUND OF THE INVENTION

This invention relates generally to dream detection systems and, more particularly, to a dream detection system having a mask to be worn by a sleeping person and a control unit that may be positioned beside a bed that enables a sleeping person to become aware that they are dreaming and to gain a certain level of control over the dream for maximum enjoyment or fulfillment.

Dreaming is considered to be desirable to most people, yet most people have difficulty recalling their dreams or may be dissatisfied when their dreams become disjointed or take uncontrollable directions. Humans have five stages of sleep: stages 1-4 and REM sleep. It is well known that the most vivid dreams occur during the Rapid Eye Movement (REM) stage of sleep. A person's brainwaves most closely resemble those of an awake person during this stage. Therefore, it is possible for a person to exert some control over the events of a dream if is made aware that he is dreaming without actually fully waking up.

Various devices have been proposed for detecting REM sleep. In fact, it has been proposed in the prior art that a person may be slightly, but not fully, awakened upon REM detection using lights or sounds so that a sleeping person may gain some control over his dream. Although assumably effective for their intended purposes, the previous proposals are prone to false detections of REM sleep and premature signaling, a lack of providing a sleeper with predetermined cues, scripts, or audible suggestions to guide the dream sequence. For example, the sleeper may be able to introduce desired people, situations, or themes into the dream sequence.

Therefore, it would be desirable to have a system that could assist a person in becoming aware of his dream and to enable him to gain an amount of control over the dream sequence. Further, it would be desirable to have a system that provides a sleeper with predetermined cues, scripts, or audible suggestions when REM sleep is detected. In addition, it would be desirable to have a system that detects REM sleep in multiple ways so as to minimize false REM detection and premature awakening procedures.

SUMMARY OF THE INVENTION

A dream detection system according to the present invention includes a mask and a control unit separate from the mask. The mask includes opaque left and right eye portions that prevent a wearer from seeing a surrounding environment. The mask may include a strap such that the mask may be removably attached to a person's head and may include a layer of pliable material for comfort when positioned on a person's face.

The mask may include one or more sensor for detecting REM sleep, one or more alarm for indicating REM sleep, and/or a speaker. The mask may also include one or more input device for adjusting the alarm or speaker, for sending test or delay signals, or for actuating other electrical components. The mask may also include a transmitter and receiver. The control unit may include a transmitter for transmitting data to the mask, a receiver for receiving data from the mask, an audio player, one or more input devices, a processor, a display, and other electronic components.

The processor in the mask includes programming for actuating the mask transmitter to transmit a signal when the mask sensor detects REM sleep. The control unit processor includes programming for actuating the audio player or other alarm components upon receiving a signal from the mask transmitter. A user may preset what audible messages will be played when the audible player is actuated. In addition, the control unit may include a microphone and data storage unit for recording a user's verbal communications, e.g. the details of a dream.

Therefore, a general object of this invention is to provide a dream detection system for making a sleeping person aware that he is dreaming so that the person may gain some control over the dream sequence.

Another object of this invention is to provide a dream detection system, as aforesaid, that provides a sleeper with predetermined cues, scripts, or audible suggestions when REM sleep is detected so as to guide the dream sequence.

Still another object of this invention is to provide a dream detection system, as aforesaid, which enables a user to audibly record details from a dream sequence for later recollection.

Yet another object of this invention is to provide a dream detection system, as aforesaid, in which a user may delay detection of REM sleep.

A further object of this invention is to provide a dream detection system, as aforesaid, which is inexpensive to manufacture and easy for a user to operate.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

A dream detection system 100 according to the present invention will now be described in detail with reference to FIGS. 1 through 7b of the accompanying drawings. More particularly, a dream detection system 100 according to the current invention includes a mask 110 and a control unit 210.

Figure 2:
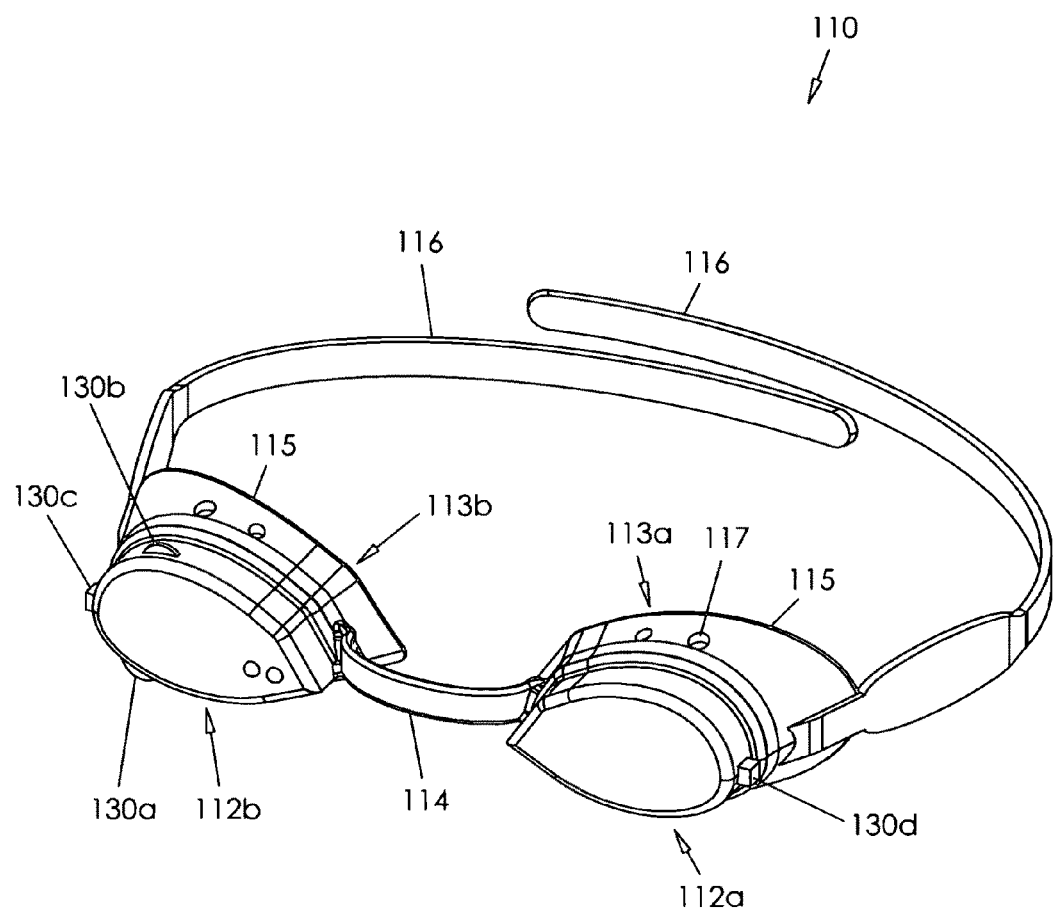
FIG. 2 is a perspective view of a mask according to the preferred embodiment of the present invention.

The mask 110 has an opaque left-eye portion 112a and an opaque right-eye portion 112b configured to collectively prevent a wearer from seeing a surrounding environment (FIG. 2). The left-eye portion 112a has an inner edge 113a, the right-eye portion 112b has an inner edge 113b, and the portions 112a, 112b may be separate (e.g., attached by strap 114 as shown in FIG. 2) or combined (e.g., similar to goggles worn for snow skiing). A layer 115 of pliable material (e.g., a silicone bead) is coupled to the inner edges 113a, 113b to provide a comfortable interface between the user and the mask 110. The layer 115 of pliable material may extend completely along the inner edge 113a of the left-eye portion 112a and the inner edge 113b of the right-eye portion 112b. Means may be included for attaching the left-eye portion 112a and the right-eye portion 112b to a human head (e.g., a user's head). More particularly, earpieces 116, a strap, or another attachment device may be operatively coupled to the left-eye portion 112a and the right-eye portion 112b. The left-eye portion 112a and the right-eye portion 112b may define vents 117 to allow fresh air to reach a user's eyes as shown in FIG. 2; care should be taken to shape and place the vents 117 so that little (if any) ambient light reaches the user.

Figure 3:
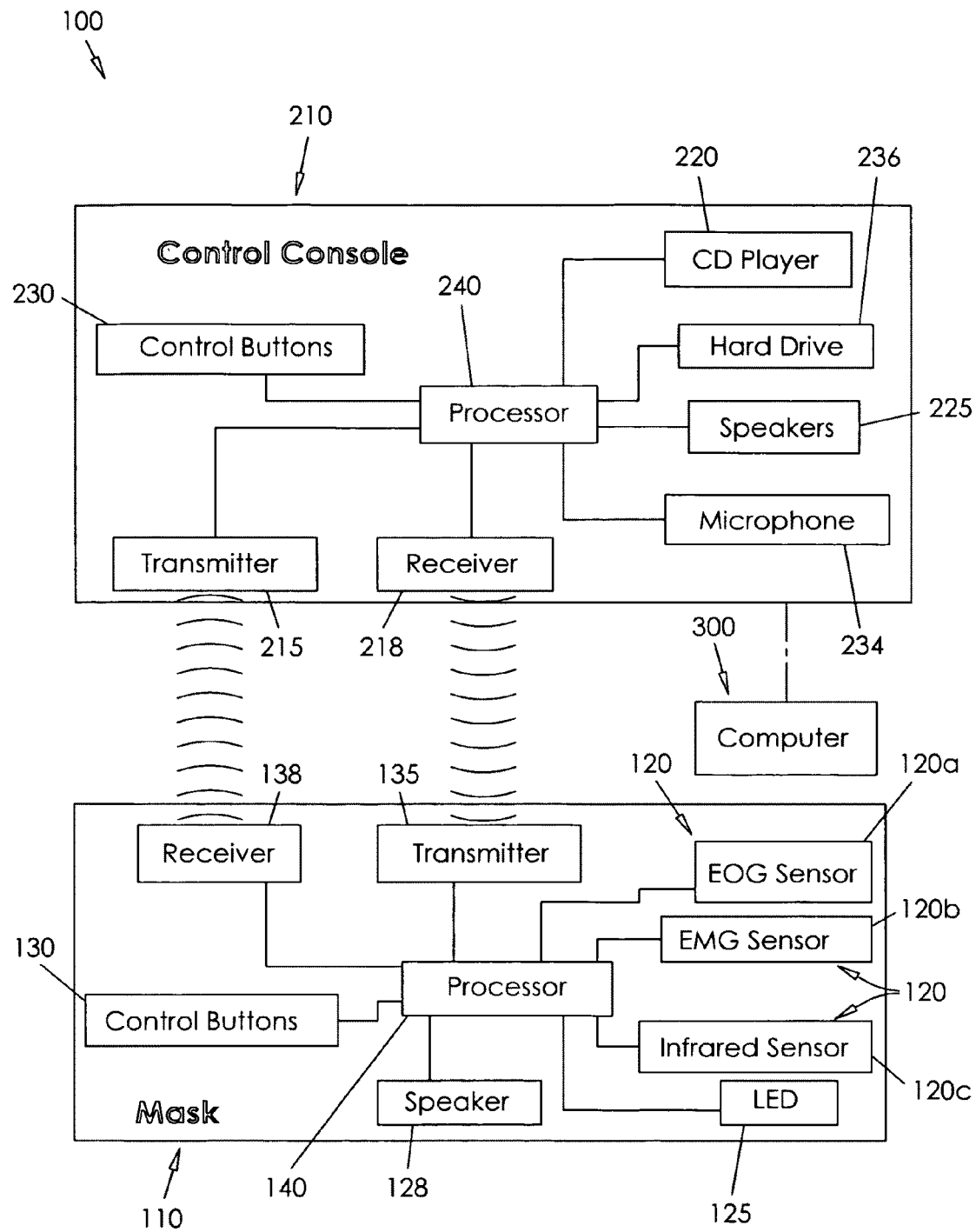
FIG. 3 is a block diagram illustrating the electrical components of the control unit and mask shown in FIGS. 1 and 2.

As shown in FIG. 3, the mask 110 may include one or more sensor 120 to detect REM sleep, one or more alarm 125 to indicate REM sleep, and/or a speaker 128. For example, the mask 110 may include an electrooculography sensor 120a, an electromyography sensor 120b, and/or an infrared sensor 120c. The infrared sensor 120c may be housed inside the left-eye portion 112a or the right-eye portion 112b; the electrooculography sensor 120a and/or the electromyography sensor 120b may be housed in the layer 115 of pliable material (e.g., inside a silicone bead). The alarm 125 may be a visual alarm and/or an audible alarm. For example, the alarm 125 may be a LED (and even more particularly, a blue LED) inside the left-eye portion 112a or the right-eye portion 112b. It is understood that multiple sensors may be used simultaneously to minimize the chances of a false indication of REM sleep so that incorrect activation of other components is likewise minimized, as will be described in more detail later.

The mask 110 may include one or more input device 130, a transmitter 135, a receiver 138, and/or a processor 140, as shown in FIG. 3. For example, an input device 130a may be included for adjusting an intensity level of the alarm 125; an input device 130b may be included for adjusting a volume output of the speaker 128; an input device 130c may be included to input a test signal; an input device 130d may be included to input a delay signal; and an input device 130e may be included to turn on the electrical components of the mask 110 (FIG. 7b). The input devices may be integrated into a single input device 130, or multiple input devices 130 may be used (as shown in FIG. 2). The processor 140 may be in data communication with the sensor(s) 120, the alarm 125, the speaker 128, the input device(s) 130, the transmitter 135, and/or the receiver 138. The processor 140 may include various programming, as described in more detail below.

Figure 1:
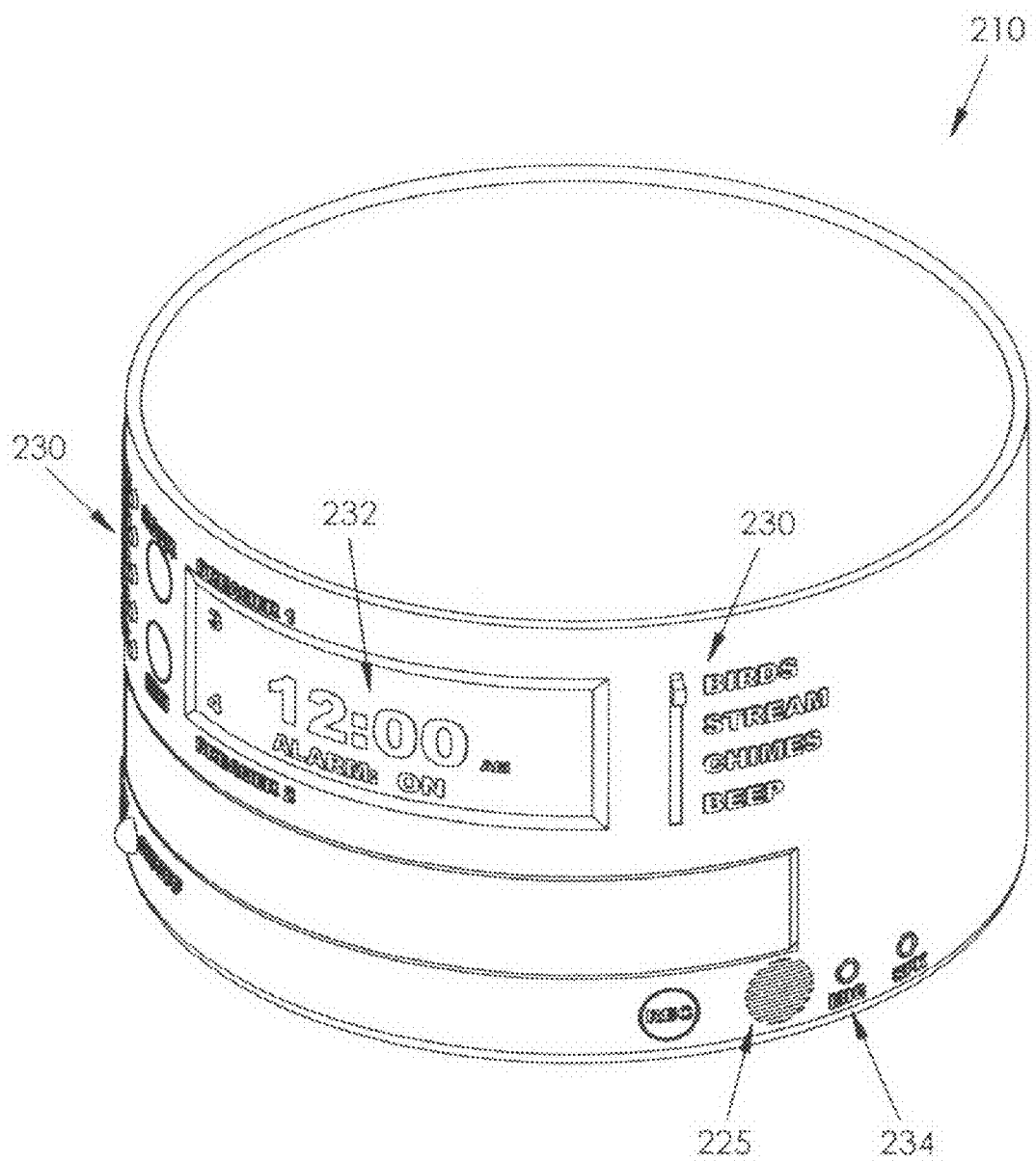
FIG. 1 is a perspective view of a control unit of a dream detection system according a preferred embodiment of the present invention.

The dream detection system 100 may further include a control unit 210 (FIG. 1) separate and distinct from the mask 110. As shown in FIGS. 1 and 3, the control unit 210 may include a transmitter 215 for transmitting data to the mask receiver 138, a receiver 218 for receiving data from the mask transmitter 135, an audio player 220 (e.g., a compact disc player or a mp3 player), a speaker 225, one or more input device 230, a display 232, a microphone 234, an electronic-data storage device 236, and/or a processor 240. The processor 240 may be in data communication with the transmitter 215, the receiver 218, the audio player 220, the speaker 225, the input device(s) 230, the display 232, the microphone 234, and/or the storage device 236. The processor 240 may include various programming, as described in more detail below.

Figure 7A:
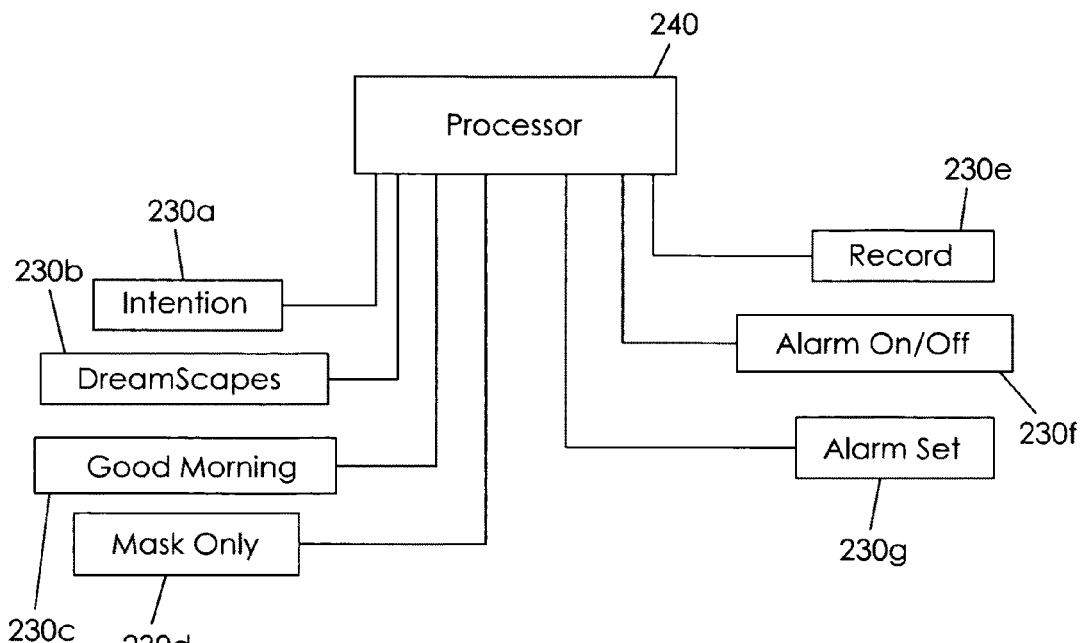
Figure 7B:
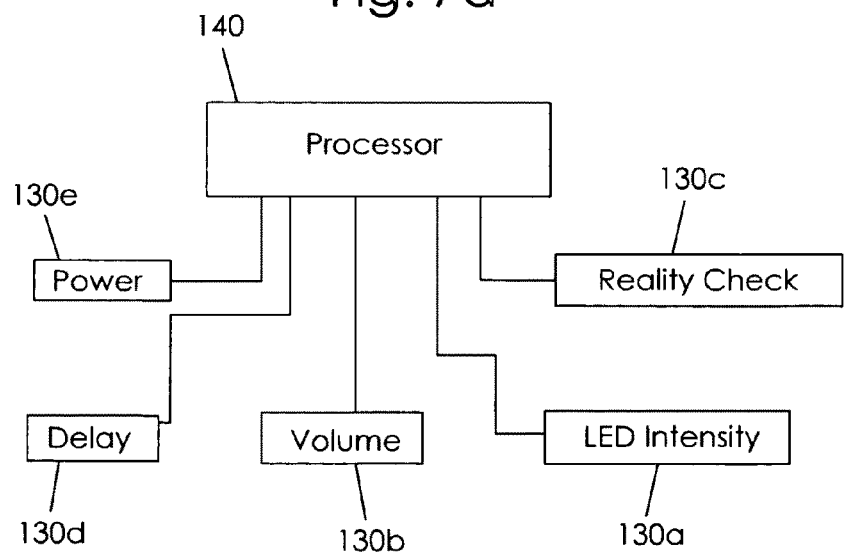

FIG. 7a shows exemplary input devices 230 that may be included. For example, an input device 230a may be included for selecting an evening affirmation/mental preparation mode; an input device 230b may be included for selecting an audible REM experience mode; an input device 230d may be included for selecting a morning affirmation mode; an input device 230d may be included for selecting a mask-only mode; an input device 230e may be included for selecting a record mode; an input device 230f may be included for selecting an alarm mode; and an input device 230g may be included to input alarm data.

Figure 4:
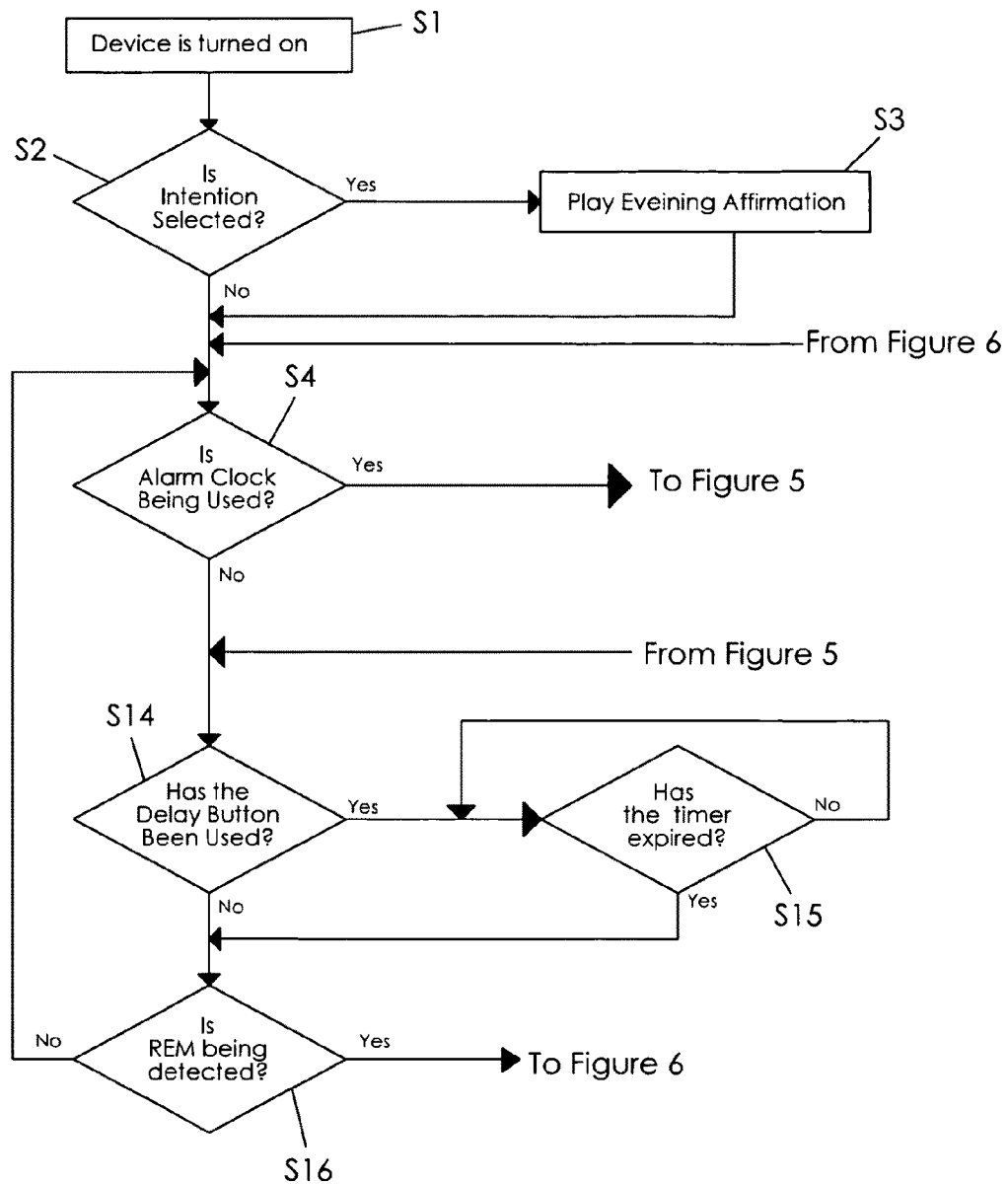
FIGS. 4-7b are flowcharts illustrating the logic performed by the dream detection system according to the preferred embodiment of the invention.
Figure 5:
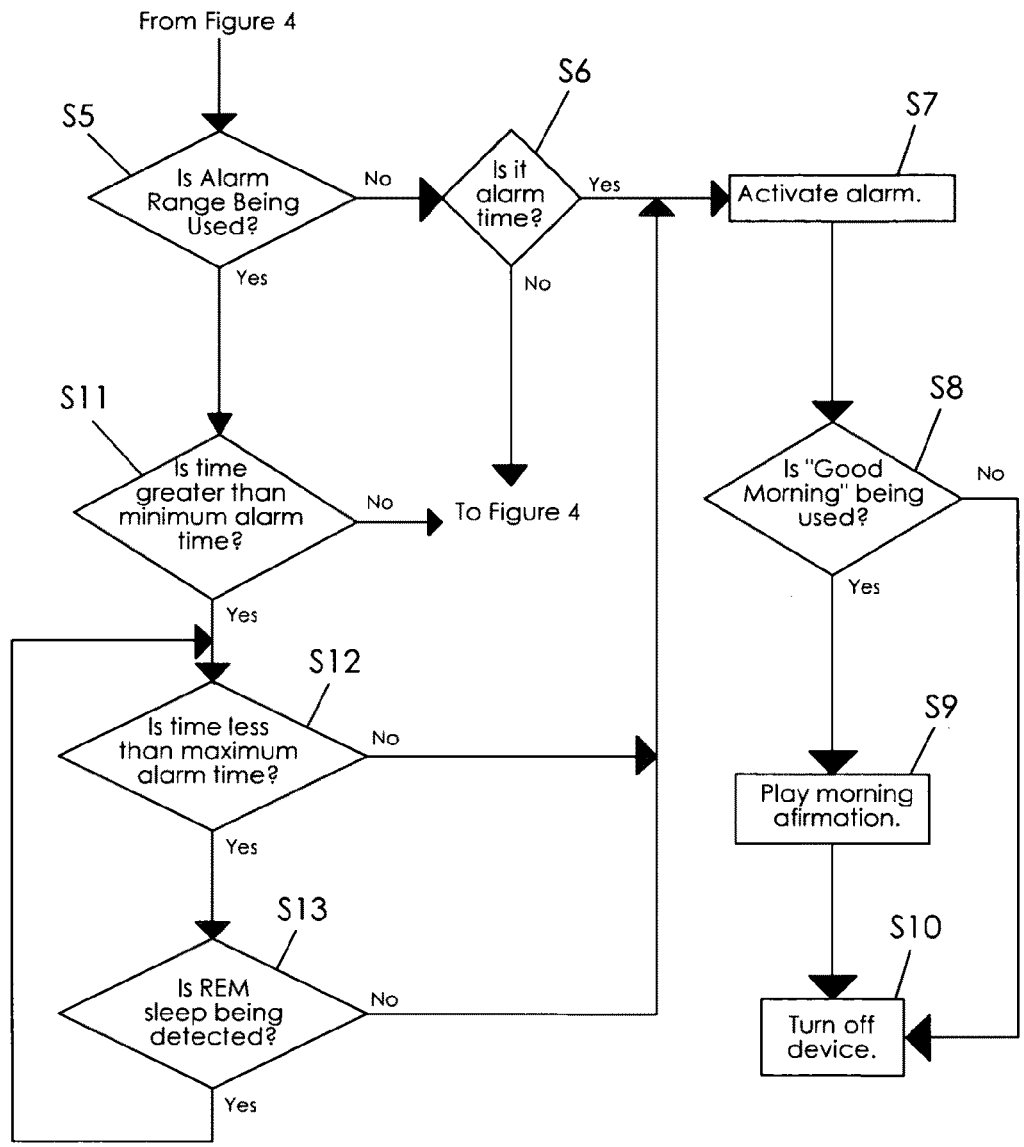
Figure 6:
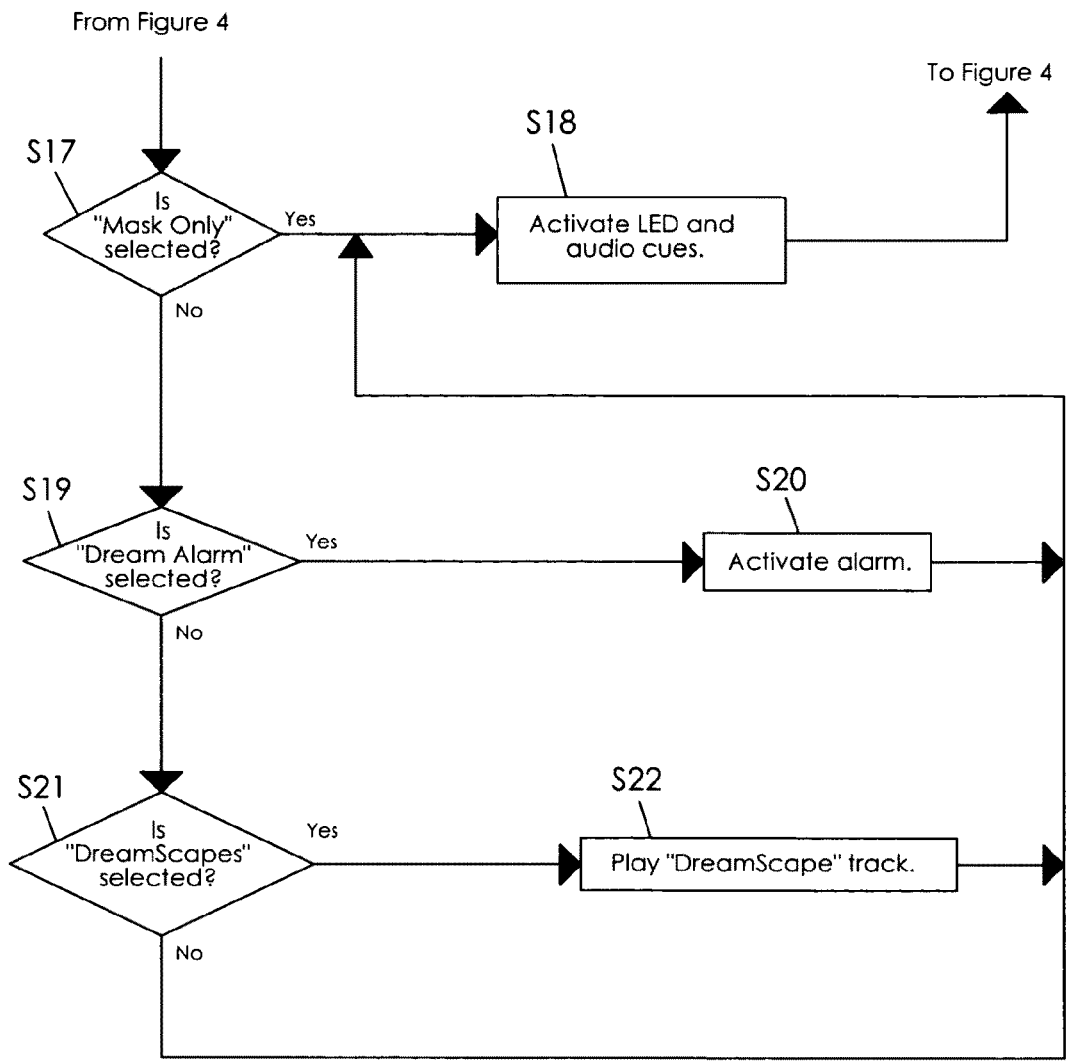

FIGS. 4 through 6 depict exemplary logic used in the dream detection system 100. At step S1, the mask 110 is turned "on" (e.g., through input device 130e), and the logic continues to step S2. At step S2, the control processor 240 determines whether the evening affirmation/mental preparation mode was selected using the input device 230a. If so, the logic proceeds to step S3; if not, the logic proceeds to step S4.

At step S3, the processor 240 uses programming for actuating the audio player 220 to output first audio data (e.g., audio data intended to relax the user and prepare the user for lucid dreaming) to actuate the audio player 220 in such a manner. This first audio data may then be broadcast through the speaker 225 or through the speaker 128 via the control transmitter 215 and the mask receiver 138. The logic proceeds to step S4.

At step S4, the processor 240 determines whether the alarm mode was selected using the input device 230f. If so, the logic proceeds to step S5 at FIG. 4. If not, the logic continues to step S14.

At step S5, the processor 240 determines whether an alarm range (having a beginning time and an ending time) was selected using the input device 230g or whether a typical alarm time was selected using the input device 230g. If an alarm range was not selected, the logic continues to step S6; if an alarm range was selected, the logic continues to step S11.

At step S6, the processor 240 determines if the alarm time has been reached. If so, the logic continues to step S7. If not, the logic proceeds to step S14 (FIG. 4) described below.

At step S7, the processor 240 actuates the speaker 225 (and/or the speaker 128 via the control transmitter 215 and the mask receiver 138) to output a wake-up-alarm and wake up the user. The logic then proceeds to step S8.

At step S8, the processor 240 determines whether the morning affirmation mode was selected using the 230d. If so, the logic proceeds to step S9. If not, the logic proceeds to step S10, where the logic ends. At step S9, the processor 240 uses programming for actuating the audio player 220 to output third audio data (e.g., audio data intended to prepare the user to have a fulfilling/successful day) to actuate the audio player 220 in such a manner. This third audio data may then be broadcast through the speaker 225 or through the speaker 128 via the control transmitter 215 and the mask receiver 138.

Returning now to step S11, the processor 240 determines if the beginning time of the alarm range has been reached. If not, the logic proceeds to step S14 (FIG. 4) described below. If so, the logic proceeds to step S12.

At step S12, the processor 240 determines if the ending time of the alarm range has been reached. If the ending time has been reached, the logic proceeds to step S7 described above. If the ending time has not been reached, the logic continues to step S13.

At step S13, the processor 240 determines whether the control receiver 218 has received a signal from the mask transmitter 135 indicating that the sensor(s) 120 detect(s) REM sleep. (The processor 140 uses programming to actuate the mask transmitter 135 to transmit a signal to the control receiver 218 upon the sensor(s) 120 detecting REM sleep.) If not, the logic proceeds to step S7 described above. If so, the logic returns to step S12. This alarm range and the logic relating to this alarm range allows a user to be awoken while he is not in REM sleep unless an ending time is reached. Because people are often groggy and less than fully rested if awoken during REM sleep, this may be extremely beneficial to a user.

Returning now to FIG. 4 and step S14, the processor 240 determines whether the input device 130d has been used to input a delay signal (the delay signal being subsequently transmitted to the control receiver 218 from the mask transmitter 135). If so, the logic proceeds to step S15; if not, the logic proceeds to step S16.

At step S15, the processor 240 determines whether the delay has expired. If so, the logic proceeds to step S16; if not, the logic returns to step S15. The delay signal and the logic relating to the delay may be useful to keep the sensor(s) 120 from falsely detecting REM sleep while the user is still awake, for example.

At step S16, the processor 240 determines whether the control receiver 218 has received a signal from the mask transmitter 135 indicating that the sensor(s) 120 detect(s) REM sleep. As noted above, the processor 140 uses programming to actuate the mask transmitter 135 to transmit a signal to the control receiver 218 upon the sensor(s) 120 detecting REM sleep. If such a signal is received by the control receiver 218, the logic proceeds to step S17 (FIG. 6); if not, the logic returns to step S4.

At step S17, the processor 240 determines whether the mask-only mode was selected using the input device 230d. If so, the logic proceeds to step S18; if not, the logic proceeds to step S19.

At step S18, the processor 240 uses programming to actuate the alarm 125 (e.g., via the control transmitter 215, the mask receiver 138, and the mask processor 140). The logic proceeds from step S18 to step S4 (FIG. 4).

At step S19, the processor 240 determines whether the input device 230e has been used to select a record mode. If so, the logic proceeds to step S20; If not, the logic proceeds to step S21.

At step S20, the processor 240 uses programming to actuate the microphone 234 and the storage device 236 to record the user's verbal communications. The logic continues from step S20 to step S18.

At step S21, the processor 240 determines whether the input device 230 has been used to select an audible REM experience mode. If so, the logic proceeds to step S22; if not, the logic continues to step S18. At step S22, the processor 240 uses programming to actuate the audio player 220 to output audio data which may include cues to help the user direct his dream in a desired direction, for example. The audio data may be output through the control speaker 225 and/or through the mask speaker 128. In other words, the control processor 240 may use programming to actuate the control transmitter 215 to transmit the audio data to the mask receiver 138, and the mask processor 140 may use programming to actuate the mask speaker 128 to output the audio data received by the mask receiver 138.

While much of the logic depicted in FIGS. 4 through 6 utilize the control processor 240 to minimize the size, weight, and power requirements associated with the mask 110, it should be understood that the mask processor 140 may alternately or additionally include programming described in relation to the control processor 240. Further, though not shown in the accompanying drawings, it should be clear that the mask processor 140 may include programming for changing an intensity level of the alarm 125 (e.g., and LED) upon user input to the input device 130a, programming for changing a volume output of the mask speaker 128 upon user input to the input device 130b, and/or programming for actuating the alarm 125 upon user input to the input device 130c. Actuating the alarm 125 using the input device 130c while the user is awake may be important in conditioning the user to understand the meaning of the alarm 125 while the user is in REM sleep. Though not described in detail herein, it should be understood that a computer 300 (FIG. 3) may be in communication with the control processor 240 (or the mask processor 140) to add additional functionality.

It is understood that while certain forms of this invention have been illustrated and described, it is not limited thereto except insofar as such limitations are included in the following claims and allowable functional equivalents thereof.

What is claimed is as follows:

1. A dream detection system, comprising:
   a mask having:
      an opaque left-eye portion and an opaque right-eye portion configured to collectively prevent a wearer from seeing a surrounding environment, said left-eye portion having an inner edge, said right-eye portion having an inner edge;
      means for attaching said left-eye portion and said right-eye portion to a human head;
      a layer of pliable material coupled to said inner edge of said left-eye portion and said inner edge of said right-eye portion, said layer of pliable material including a silicone bead extending completely along said inner edge of said left-eye portion and said inner edge of said right-eye portion;
      a first input device;
      an infrared sensor positioned in one of said left-eye portion or said right-eye portion to detect REM sleep;
      an electromyography sensor housed in said silicone bead to detect REM sleep;
      an alarm to indicate REM sleep;
      a first transmitter;
      a first receiver; and
      a first processor in data communication with said first input device, said sensor, said alarm, said first transmitter, and said first receiver;
   a control unit separate and distinct from said mask, said control unit having:
      a second transmitter for transmitting data to the first receiver;
      a second receiver for receiving data from the first transmitter;
      an audio player;
      a speaker;
      a second input device;
      a second processor in data communication with said second transmitter, said second receiver, said audio-player, said speaker, and said second input device;
      a microphone and an electronic-data storage device;
      said second processor is in data communication with said microphone and said storage device;
   wherein:
      said first processor has programming for actuating said first transmitter to transmit a signal to said second receiver upon said sensor detecting REM sleep; and
      said second processor has programming for actuating said microphone and said storage device upon receipt of said signal by said second receiver.

2. The system of claim 1, wherein:
   said first processor has programming for actuating said first transmitter to transmit a signal to said second receiver upon said sensor detecting REM sleep; and
   said second processor has programming for actuating said audio player upon receipt of said signal by said second receiver.

3. The system of claim 1, wherein said alarm is a LED inside one of said left-eye portion and said right-eye portion.

4. The system of claim 3, wherein:
said first processor includes programming for changing an intensity level of said LED upon user input to said first input device;
one of said first processor and said second processor includes programming for actuating said LED upon said sensor detecting REM sleep;
said first processor has programming for actuating said first transmitter to transmit a signal to said second receiver upon said sensor detecting REM sleep;
said second processor has programming for actuating said audio player upon receipt of said signal by said second receiver and actuating said second transmitter to transmit audio data from said audio player to said first receiver;
said mask further comprises a mask speaker and a volume input device;
said first processor includes programming for actuating said mask speaker to output said audio data received by said first receiver; and
said first processor includes programming for changing a volume output of said mask speaker upon user input to said volume input device.

5. The system of claim 3, wherein said first processor has programming for actuating said LED upon user input to said first input device.

6. The system of claim 1, wherein said first processor has programming for delaying detection of REM sleep by said sensor for a predetermined period of time upon user input to said first input device.

7. The system of claim 1, wherein:
said first processor has programming for actuating said first transmitter to transmit a signal to said second receiver upon said sensor detecting REM sleep;
said second processor has programming for actuating said speaker during a predetermined alarm range having a beginning time and an ending time; and
said second processor has programming for not actuating said speaker while said REM sleep is detected by said sensor unless said REM sleep is detected at said ending time.

8. The system of claim 7, wherein:
said second processor has programming for actuating said audio player to output first audio data before receipt of said signal by said second receiver;
said second processor has programming for actuating said audio player to output second audio data upon receipt of said signal by said second receiver; and
said second processor has programming for actuating said audio player to output third audio data after actuating said speaker during said predetermined alarm range.

9. A dream detection system, comprising:
a mask having:
an opaque left-eye portion and an opaque right eye portion configured to collectively prevent a wearer from seeing a surrounding environment, said left-eye portion having an inner edge, said right-eye portion having an inner edge;
means for attaching said left-eye portion and said right-eye portion to a human head;
a layer of pliable material coupled to said inner edge of said left-eye portion and said inner edge of said right-eye portion, wherein said layer of pliable material includes a silicone bead extending completely along said inner edge of said left-eye portion and said inner edge of said right-eye portion;
a first input device;
one or more sensors to detect REM sleep;
wherein one of said one or more sensors is an infrared sensor positioned in one of said left-eye portion or said right-eye portion to detect REM sleep;
wherein another of said one or more sensors is selected from the group consisting of an electrooculography sensor and an electromyography sensor and housed in said silicone bead;
an alarm to indicate REM sleep;
a processor in data communication with said first input device, said sensor, and said alarm;
wherein said first processor includes programming for actuating said alarm upon said sensor detecting REM sleep;
a first transmitter and a first receiver;
wherein said first processor is in data communication with said first transmitter and said first receiver;
a control unit separate and distinct from said mask, said control unit having:
a second transmitter for transmitting data to the first receiver;
a second receiver for receiving data from the first transmitter;
an audio player;
a speaker;
a second input device; and
a second processor in data communication with said second transmitter, said second receiver, said audio-player, said speaker, and said second input device.

10. The system of claim 9, wherein said one or more sensors to detect REM sleep includes both said electrooculography sensor and said electromyography sensor positioned in said bead.

11. The system of claim 9, wherein:
said first processor has programming for actuating said first transmitter to transmit a signal to said second receiver upon said sensor detecting REM sleep;
said second processor has programming for actuating said speaker to output a wake-up-alarm sound during a predetermined alarm range having a beginning time and an ending time; and
said second processor has programming for not actuating said speaker to output said wake-up-alarm sound while said REM sleep is detected by said sensor unless said REM sleep is detected at said ending time.

* * * * *